US008306290B2

(12) United States Patent
Parks

(10) Patent No.: US 8,306,290 B2
(45) Date of Patent: Nov. 6, 2012

(54) DIAGNOSTIC SYSTEM FOR DISPLAY OF HIGH-RESOLUTION PHYSIOLOGICAL DATA OF MULTIPLE PROPERTIES

(75) Inventor: Thomas R. Parks, Hermosa Beach, CA (US)

(73) Assignee: Sierra Scientific Instruments, LLC, Los Angeles, CA (US)

( * ) Notice: Subject to any disclaimer, the term of this patent is extended or adjusted under 35 U.S.C. 154(b) by 1111 days.

(21) Appl. No.: 12/148,679

(22) Filed: Apr. 20, 2008

(65) Prior Publication Data

US 2009/0003669 A1 Jan. 1, 2009

Related U.S. Application Data

(60) Provisional application No. 60/925,541, filed on Apr. 20, 2007.

(51) Int. Cl.
*A61B 5/00* (2006.01)
*G06K 9/20* (2006.01)
*A61B 5/103* (2006.01)

(52) U.S. Cl. ........ 382/128; 382/284; 382/286; 382/294; 600/463; 600/593

(58) Field of Classification Search .......... 382/128–133, 382/284–294; 600/301, 407–464
See application file for complete search history.

(56) References Cited

U.S. PATENT DOCUMENTS

| 4,774,956 A | 10/1988 | Kruse et al. |
| 5,024,240 A | 6/1991 | McConnel |
| 5,117,827 A | 6/1992 | Stuebe et al. |
| 5,438,985 A | 8/1995 | Essen-Moller |
| 5,479,935 A | 1/1996 | Essen-Moller |
| 5,533,515 A | 7/1996 | Coller et al. |
| 6,104,941 A | 8/2000 | Huey et al. |
| 6,740,047 B2 | 5/2004 | Holmes et al. |
| 7,215,338 B2 | 5/2007 | Horn et al. |
| 7,236,820 B2 * | 6/2007 | Mabary et al. ........... 600/547 |
| 2003/0028088 A1 | 2/2003 | Castell et al. |
| 2003/0077223 A1 | 4/2003 | Glukhovsky et al. |
| 2003/0135120 A1 * | 7/2003 | Parks et al. ........... 600/463 |

(Continued)

FOREIGN PATENT DOCUMENTS

JP 2006-523517 A 10/2006

(Continued)

OTHER PUBLICATIONS

American Journal of Physiology vol. 288 May 2005, "Bolus transit pattern in health subjects", hala Imam et al.*

(Continued)

*Primary Examiner* — Melissa Koval
*Assistant Examiner* — Emily Chan
(74) *Attorney, Agent, or Firm* — Wolf, Greenfield & Sacks, P.C.

(57) ABSTRACT

A diagnostic system for display of physiological data in a format useful for identifying or diagnosing physiological conditions. The system registers visual representations of different types of physiological data to aid in an understanding of bodily processes. In addition to registering the data, the system may display different types of physiological data with different visual characteristics. Further, the transparency of the visual representations of the different datasets may be controlled to enhance the understandability of displayed information. The system, for example, can be used with data representative of pressure and impedance within a patient's gastrointestinal tract to provide greater understanding of physiological processes during a swallow.

39 Claims, 11 Drawing Sheets

U.S. PATENT DOCUMENTS

| | | | |
|---|---|---|---|
| 2003/0144604 A1 | 7/2003 | Holmes et al. | |
| 2004/0143182 A1 | 7/2004 | Kucera et al. | |
| 2005/0065450 A1 | 3/2005 | Stuebe et al. | |
| 2005/0080832 A1 | 4/2005 | Stuebe et al. | |
| 2005/0148884 A1 | 7/2005 | Parks et al. | |
| 2005/0228308 A1 | 10/2005 | Iddan et al. | |
| 2006/0004304 A1* | 1/2006 | Parks | 600/593 |
| 2006/0052702 A1* | 3/2006 | Matsumura et al. | 600/443 |
| 2006/0164511 A1 | 7/2006 | Krupnik | |
| 2006/0169294 A1 | 8/2006 | Kaler et al. | |
| 2007/0060798 A1 | 3/2007 | Krupnik et al. | |
| 2007/0276196 A1* | 11/2007 | Donaldson et al. | 600/300 |
| 2009/0257554 A1* | 10/2009 | Parks | 378/44 |

FOREIGN PATENT DOCUMENTS

| | | |
|---|---|---|
| JP | 2007-535983 A | 12/2007 |
| KR | 10-2006-0031799 A | 4/2006 |

OTHER PUBLICATIONS

International Search Report and Written Opinion mailed Aug. 20, 2008 for International Application No. PCT/US20081005120 (10 pages).

Chinese Office Action dated Apr. 26, 2011 for Application No. 200880020702.9.

\* cited by examiner

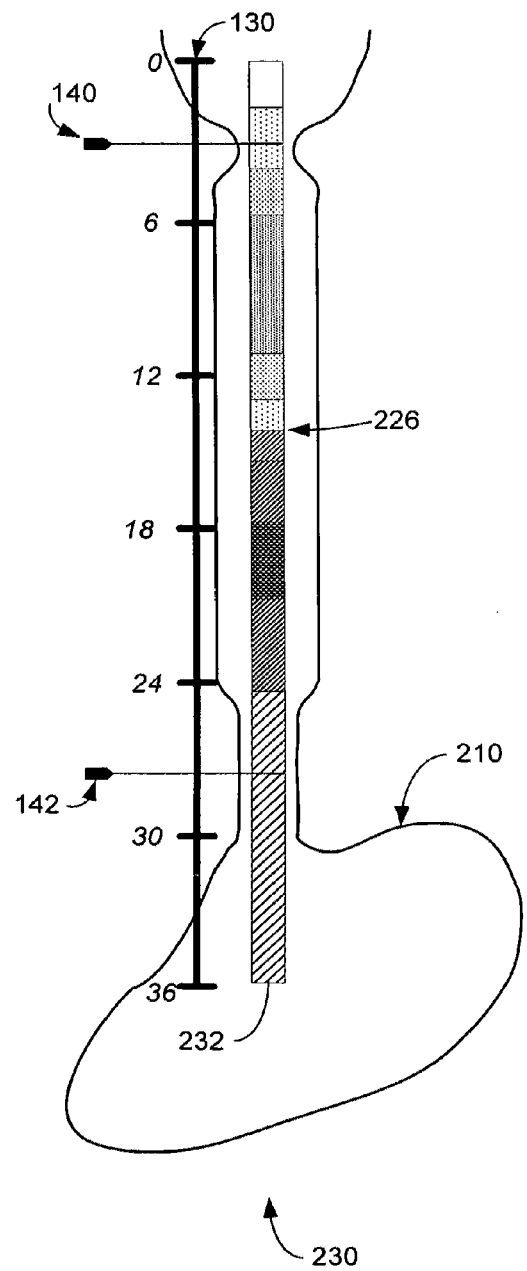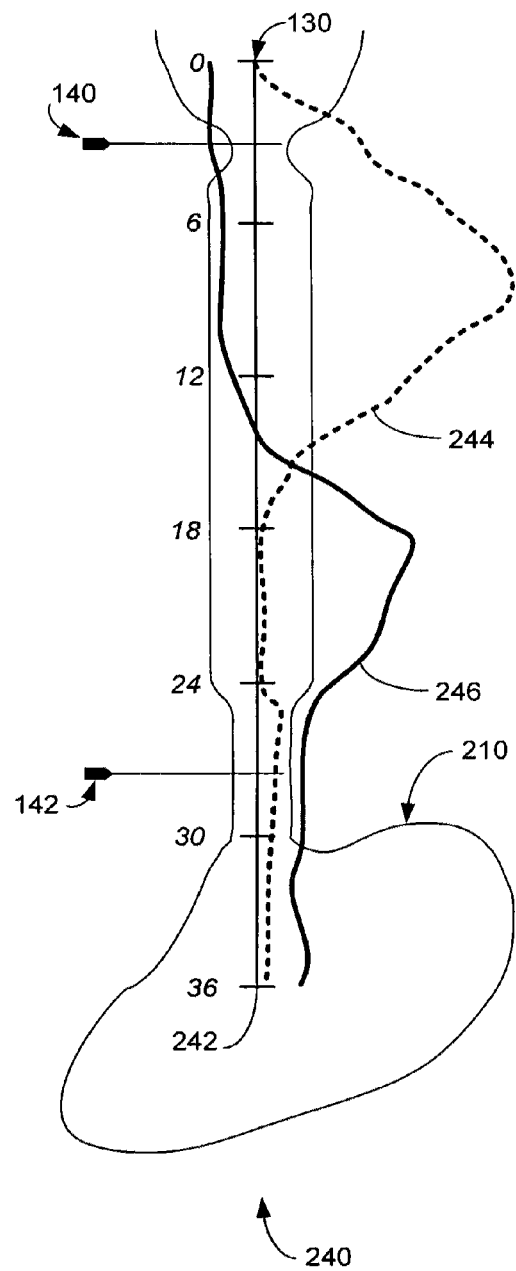

DIAGNOSTIC SYSTEM FOR DISPLAY OF HIGH-RESOLUTION PHYSIOLOGICAL DATA OF MULTIPLE PROPERTIES

CROSS-REFERENCE TO RELATED APPLICATION

The present application claims the benefit, under 35 U.S.C. §119(e), of U.S. Provisional Application Ser. No. 60/925,541, filed Apr. 20, 2007, entitled "Method for Display of High-Resolution Physiological Data of Multiple Properties," which application is hereby incorporated herein by reference.

BACKGROUND

The esophagus is a tubular organ that carries food and liquid from the throat to the stomach. Accurate measurements of physiological parameters of the esophagus under realistic swallowing conditions are valuable in diagnosing esophageal diseases such as Achalasia, dysphagia, diffuse esophageal spasm, ineffective esophageal motility, and hypertensive lower esophageal sphincter (LES). When a person with a healthy esophagus swallows, circular muscles in the esophagus contract. The contractions begin at the upper end of the esophagus and propagate downwardly toward the lower esophageal sphincter (LES). The function of the peristaltic muscle contractions, i.e., to propel food and drinks through the esophagus to the stomach, is sometimes called the motility function, but is also often referred to as peristalsis.

An upper esophageal sphincter (UES) is located at an upper end of the esophagus. The UES is a muscle that serves as a valve between the esophagus and the pharynx from which the esophagus receives food and liquid when swallowing.

The lower esophageal sphincter (LES) is located at a lower end of the esophagus. The LES is a muscle that serves as a valve between the esophagus and the stomach. The LES protects the lower esophagus from stomach acid and bile, which causes the discomfort of heartburn and in time can damage or scar the esophagus.

The LES is normally closed, but it opens momentarily when a peristaltic contraction approaches it to admit any swallowed volume of food or drink, which is called a "bolus," into the stomach. As a peristaltic contraction passes through each point along the esophagus, the esophageal pressure at that point rises to a maximum and then falls back to a base pressure at the relaxed state. This peristaltic propagation of the esophageal contraction tends to propel the "bolus," ahead of the point of peak pressure and down the esophagus toward the stomach. The motility function of the esophagus, i.e., the esophagus' ability to move a mass, is dependent on several factors, including the peristaltic pressure profile and the characteristics of the esophageal muscles.

Esophageal pressure measurement, or manometry, as well as electrical impedance have been used to assess motility function of the esophagus and bolus transit dynamics in the esophagus. A typical esophageal manometer includes an elongated catheter or probe with pressure sensors located along its length. The catheter or probe is designed to be inserted into the esophagus, typically reaching the LES and extending into the stomach of a patient, with the pressure sensors positioned at the LES and at a plurality of other specific points along the length of the esophagus at predetermined distances above the LES. During a typical test, the patient swallows a specific amount of water with the manometer placed in the esophagus. The esophageal pressure at the pressure sensors can be measured and used as an indication of the magnitude and sequence of the peristaltic contractions. In addition, because the positions of the sensors are known, the velocity of the peristaltic motion can also be ascertained from the location of the peak pressure, or onset of pressure rise, at each location as a function of time. The test can be repeated a number of times to obtain a set of pressure and velocity values, a statistical analysis of which may be used for diagnostic purposes.

High-resolution manometry involves collection of data with a catheter having closely spaced sensors. Such high-resolution data enables spatiotemporal contour plots visualization of contractile pressure physiology. Products such as ManoScan™ data acquisition software and ManoView™ data analysis software may be used to aid in visualizing high-resolution manometry data.

High-resolution impedance has also been researched independently and also provides for spatiotemporal plotting of bolus movement. Electrical impedance at a plurality of points in the esophagus can be used to detect and monitor movement of a bolus through the esophagus. A bolus of water or food will have different electrical impedance than the non-filled esophagus, so a change in impedance in the esophagus indicates presence of a bolus. Therefore, an elongated probe positioned in the esophagus with a plurality of impedance and/or acidity sensors dispersed along its length can be used to detect and monitor the bolus transit, i.e., the movement of a bolus through the esophagus.

SUMMARY

A system and method for display of high-resolution physiological data of multiple properties is provided.

In some aspects, the invention relates to a method of displaying physiological data relating to a bodily lumen. The method comprises a first providing step, a second providing step, a correlating step, a selecting step, and a displaying step. The first providing step comprises providing a first dataset, the first dataset comprising a plurality of data values relating to a first property along the lumen during a time interval. The second providing step comprises providing a second dataset, the second dataset comprising a plurality of data values relating to a second property along the lumen during the time interval. The correlating step comprises correlating the first dataset and the second dataset in space and time. The selected step comprises a portion of the first dataset and a portion of the second dataset based on data values of the second dataset. Finally, the displaying step comprises displaying on a plot, at least the selected portion of the first dataset and at least the selected portion of the second dataset as correlated in space and time, the selected portion of the second dataset being displayed using a representation that is visually distinct from a representation of the selected portion of the first dataset.

In another aspect, the invention relates to a computer storage medium encoded with instructions that, when executed, perform a method for displaying physiological data. As part of the method, a first dataset and a second dataset are obtained. The first dataset and the second dataset comprise measurements of different physiological properties in a shared spatial region. A transparency for the second dataset within at least a portion of the shared spatial region is determined, and a composite image is formed with a visual representation of the first and second datasets based on the transparency. The composite image is then displayed.

In yet another aspect, the invention relates to a system for displaying physiological data related to a bodily lumen. The system comprises a data source, a computer, and a display. The data source is a source of physiological data in the form of a first dataset and a second dataset, the first dataset and the second dataset comprising measurements of different physiological properties in a shared spatial region. The computer receives the first dataset and second dataset from the data source and outputs a composite image. The computer has a determining module that calculates a transparency for the second dataset within at least a portion of the shared spatial region and a compositing module for forming a composite image representing the first dataset and the second dataset based on the transparency value. Finally, the display displays the composite image output from the computer.

BRIEF DESCRIPTION OF DRAWINGS

The invention and embodiments thereof will be better understood when the following detailed description is read in conjunction with the accompanying drawing figures. In the figures, elements are not necessarily drawn to scale. In general, like elements appearing in multiple figures are identified by a like reference designation. In the drawings:

FIG. 2C is an embodiment with two datasets displayed, each according to a respective color map, on a single plot with one coordinate axis;

FIG. 2D is an embodiment with two datasets displayed as data lines on a single plot with one coordinate axis;

DETAILED DESCRIPTION

Figure 1:
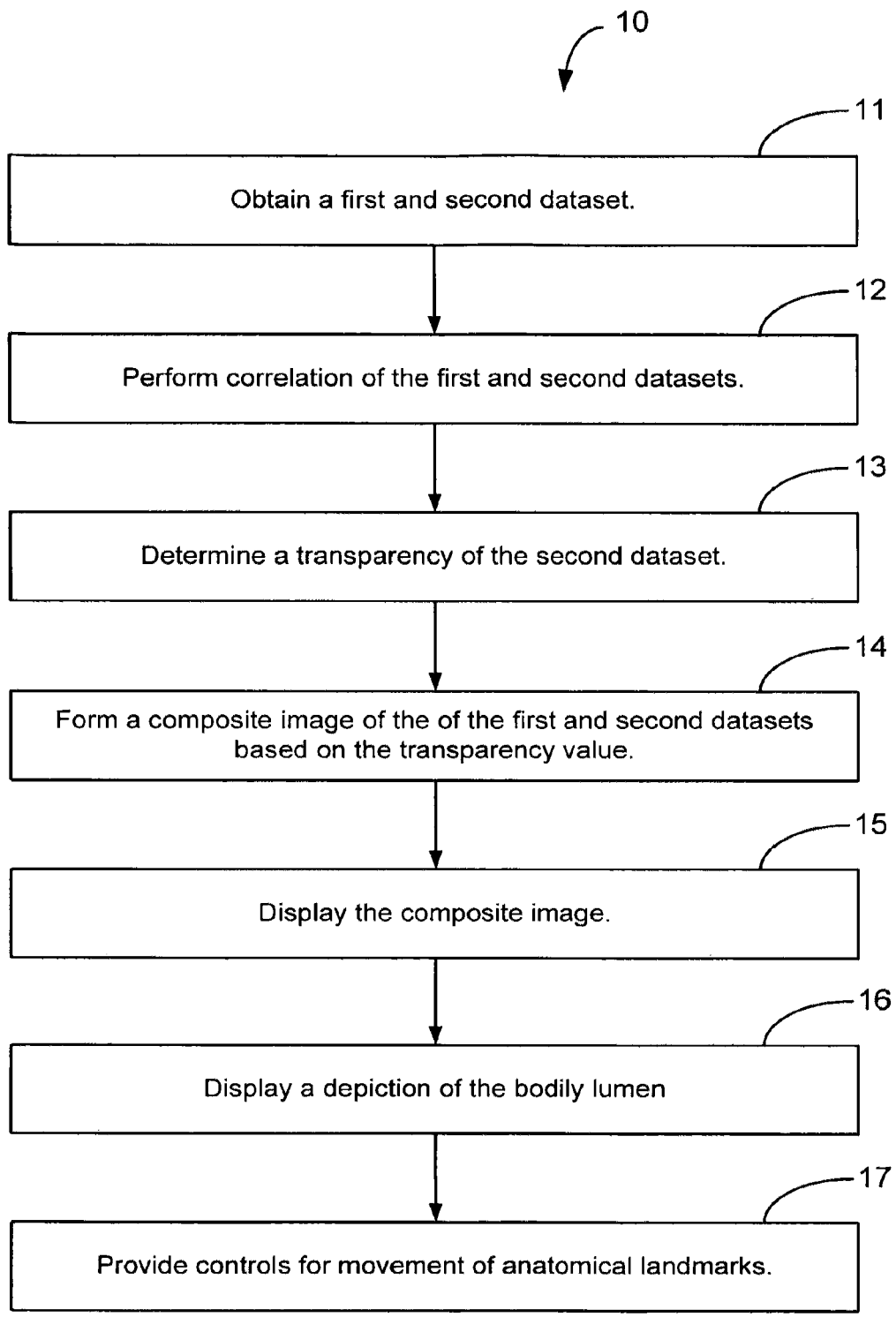
FIG. 1 is a method of operating a computing device to display data.

The inventors have recognized and appreciated that manometry data and impedance measurements indicating bolus position provide adjunctive information. The two measurements, when properly displayed together, provide a more complete picture of the physiology of an organism. Though manometry provides information about the contractile pressures that normally drive a bolus and identify the opening and closing of the UES and LES, in certain situations, manometry alone may not provide sufficient information to understand the movement of bolus necessary to make a definitive diagnosis of certain disorders, such as diffuse esophageal spasm or ineffective esophageal motility. By co-registering high-resolution manometry and impedance data sets in both time and position, the precise interaction between contractile pressure and bolus movement can be precisely and intuitively visualized in a way that is not possible by visualizing these two data sets independently. This enables a more reliable diagnosis of certain motility disorders.

The inventors have also recognized and appreciated that these two types of data can be effectively superimposed as contour plots. The plots can be formed by displaying bolus measurement values for low bolus signal strength as partially or wholly transparent so that the underlying pressure values in co-registered contour plots. This approach is made tenable through the observation the bolus and contractile pressure are largely mutually exclusive, i.e. contractile pressures tend to displace the bolus, thus the pressure data is largely visible through the bolus contour plot.

The inventors have recognized and appreciated that the method used to display physiological data can impact the ease with which medical diagnoses or other data analysis may be performed. To provide improved presentation of physiological data, a diagnostic system may display high-resolution physiological data of a second property superimposed on data of a first property in a way that is accurately distributed spatially and synchronized temporally. Such a system may be used for data collected along a tubular organ of the body having an axial direction, and the data may be distributed in the axial direction. These data may be superimposed on both a profile display (instantaneous distribution of values along the axial direction) and on a spatiotemporal display (time history of that distribution). In some embodiments, at least a portion of the plot of the second property is at least partially transparent to allow the data of the first property to be viewed concurrently. Further, the data may be used to identify anatomical landmarks using the high-resolution data signatures so that the system can depict the data relative to a depiction of the anatomy in a way that is spatially accurate.

In an example embodiment, the diagnostic systems displays high-resolution manometry data as the first physiological property with superimposed data indicating a position of a gastrointestinal bolus, such as with high-resolution conductance or impedance measurements, as the second physiological property. The diagnostic system allows for an intuitive visualization of gastrointestinal motility and other visceral processes that are suitable for measurement along some axial (longitudinal) dimension. By superimposing the physiological data in a spatially co-registered fashion, the interpretation of these data are made qualitatively more intuitive. Superposition in a spatiotemporal plane is helpful in visualizing both the instantaneous relationship between the properties and the time history of this relationship. The intuitive aspects of this visualization method are further enhanced by the registration of these spatially correlated data with the anatomy as identified from the anatomical signatures within the high-resolution data itself. Thus, the data are presented correctly relative to the anatomical landmarks and to one another.

The physiological data of the first property may be stored as a first dataset and the physiological data of the second property may be stored as a second dataset. The physiological data may come from data collected inside the esophagus, other portions of the GI tract, the urinary tract, the vascular network, and other visceral systems in which high-resolution measurements of more than one physical property are made extending along at least one spatial dimension. Though, some embodiments may have applications beyond the presentation of physiological data to other types of appropriate datasets.

Different embodiments may provide a useful way to display physiological datasets having two, three, or more degrees of freedom. Here a degree of freedom is counted for each axis used to specify a coordinate of a data value and for the data value itself. In an embodiment in which datasets are collected by sampling the outputs of sensors positioned along a catheter, the position of a sensor along a catheter and the time of a manometry or conductance measurement represent two of the degrees of freedom. The measurement, such as pressure or conductance, represents a third degree of freedom.

According to some embodiments a display may be formed according to the method 10 in FIG. 1. Method 10 comprises steps 11 through 17, which may be performed in any order to the extent permitted by the dependency of the steps. Some steps may be optionally performed. Displays resulting from using exemplary embodiments of method 10 are shown in FIGS. 2B-2E and FIGS. 5-8 and referred to for illustration of the method. The embodiments shown in these drawings are described in detail following the description of method 10.

In step 11 a first dataset and a second dataset are obtained. The datasets may include high-resolution data acquired from a computer storage device, directly from a measurement apparatus, or by any other suitable means of acquiring data. At least a portion of both datasets correspond to the same spatial region, and the spatial relationship between the measurement sites of the two properties may be known.

Further, a time relationship between the data sets is also determinable. In some embodiments, measurements for both data sets may be taken synchronously. In other embodiments, timestamp for each measurement may be included in the datasets. Though, any other suitable mechanism may be used to relate the values in each data set during period of time over which both data sets are collected.

In the example embodiment, the first and second datasets represent pressure and conductance measurements, respectively, taken inside a bodily lumen, such as the esophagus, as measured by respective and closely spaced sensors along the length of a catheter. Electronics may perform measurements using these sensors and store the resulting data as first and second datasets. In some embodiments the electronics provide time information such as a time stamp or by synchronous data sampling. In yet other embodiments, time information can be conveyed by providing a start or end time of the data set. This information, along with knowledge of sampling rate, allows one to synchronize the two data sets. The pressure dataset and conductance dataset in this example embodiment may both have three degrees of freedom: a measurement time coordinate, a measurement position coordinate (such as a position along the catheter), and a measurement value. However, the invention is not limited to use in conjunction with these specific properties. For example, in some other embodiments the datasets represent any of temperature, acidity (pH), radiographic data, or any other measurable parameter.

In step 12 correlation of the first and second datasets is performed. Correlation, for example, may include time synchronization. Correlation ensures that shared degrees of freedom, (e.g., time, position) between the first and second dataset, are in alignment with one another. For example, if both datasets have time as a coordinate axis, the relative times may be synchronized to a single reference timer so that simultaneous events in the first and second dataset have the same reference time. Correlation ensures that measurements from both datasets are properly registered with the coordinate system.

Similarly, if the spatial relationship between measurements sites of the two properties is not stored in the datasets, the positions may be correlated.

In some embodiments, datasets may be correlated based on the manner in which the data is acquired. For example, datasets may be spatially correlated based on a predetermined spatial relationships of sensors used to collect the first and second data sets. The data sets may be correlated in time through the use of correlated sampling times. Accordingly, process at step 12 may not entail explicit data manipulation.

To determine how the second dataset is superimposed on the first dataset, a transparency is determined in step 13. The transparency determines the visibility of the second dataset when superimposed on the first. The inventors have recognized and appreciated that for certain types of physiological properties, selecting a transparency, which may be different for different portions of the second dataset or may be different at different times, can allow display of physiological data in a way that allows a human viewer of the information to better understand the physiological processes represented in the data. For example, the data in plot 300 in (FIG. 3), representing a manometry measurement, and the data in plot 400 (FIG. 4), representing conductance, each only take large values when the other is small (see legend 100 in FIG. 2A). These figures provide an example of a scenario in which important information content of the second dataset may be substantially mutually exclusive to the important information content of the first dataset.

Thus, in some embodiments, transparency transformation captures which portion or portions of the second dataset contain important information and may be used to determine which portion of each dataset is used in generating a display. For example, in some embodiments it is preferable to display the second dataset with greatest transparency at coordinates where the data value is at a minimum and with least transparency (greatest opacity) at coordinates where the data value is at a maximum. The transparency at coordinates where the second dataset is at an intermediate value may be proportional to said value. For example, plot 820 (FIG. 8) shows a second dataset, represented by monochromatic color map, which appears to be superimposed over a first dataset when transparency is determined in this way.

Figure 2A:
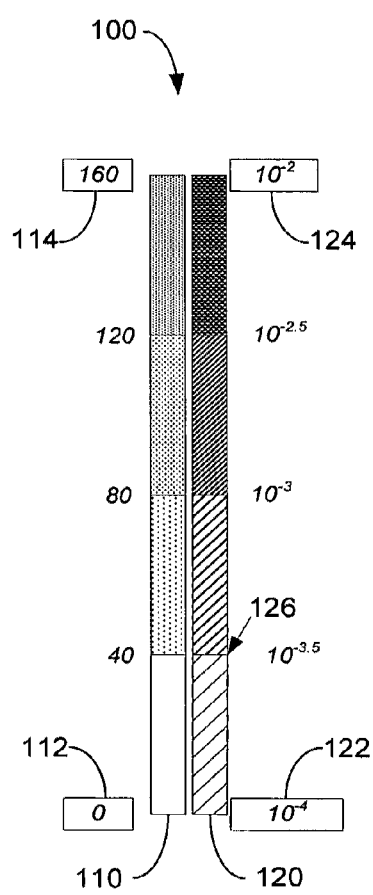
FIG. 2A is a plot legend according to some embodiments.

According to some embodiments, the transparency serves to weight the display at a coordinate towards either the first dataset (when the transparency value more closely represents a fully transparent state than an opaque state) or the second dataset (when the transparency value more closely represents an opaque state than a fully transparent state). In an example embodiment, the transparency at a coordinate is proportional to the value of the second dataset at the coordinate relative to its position between a minimum value and maximum value. The minimum value and maximum value may be user selected or determined by the second dataset directly. For example, a user may select the maximum value of the second dataset with upper limit control 124 and the minimum value of the second dataset with lower limit control 122 of legend 100 (FIG. 2A). If the coordinate corresponds to a point of minimum value, the transparency represents a fully transparent state; if the coordinate corresponds to a point of maximum value, the transparency represents an opaque state; and if the coordinate corresponds to a point with an intermediate value, the transparency represents a translucent, or semi-see-through state.

According to some embodiments, the transparency of the second dataset at each coordinate location may be based on the data value of the second dataset at said coordinate location. In another example embodiment, a threshold value is selected between the minimum value and maximum value (absolute, or user selected) in the second dataset. In regions where the data values of the second dataset are above the upper threshold, the data values of the second dataset are represented without transparency. In regions where the data values of the second dataset are below the lower threshold, the data values of the second dataset are fully transparent (i.e., invisible) and the representation of the data values of the first dataset are visible. For example, embodiment 500 (FIG. 5) shows the second dataset (plotted independently in plot 400, FIG. 4) in regions where the data values are above threshold 126 (in legend 100, FIG. 2A) and shows the first dataset (plotted independently in plot 300, FIG. 3) otherwise.

One of skill in the art should understand that, as used herein, "above" and "below" are relative terms. "Above" signifies the direction in which measurements at a location change when a bolus arrives at that location and "below" signifies the direction in which measurements at a location change as a bolus leaves a location.

In yet another example embodiment, a set of contour values may be selected for displaying the second dataset. The transparency at coordinates where the second dataset has a value equal to one of the contour values is highly opaque. Otherwise, the transparency may permit the first dataset to be visible. (See embodiment 600, FIG. 6.)

In still yet another embodiment, the transparency may be determined by a dithering pattern. The dithering pattern may be a random or predetermined pattern. In some embodiments, the transparency may dither between indicating that the second dataset should be displayed with a highly transparent representation and indicating that the second dataset should be displayed with a highly opaque representation.

The transparency of the second dataset may be determined according to any of the above example embodiments, or in any way suitable for combining the datasets into a single image for display. The transparency may be determined for some or all of the portion of the second dataset to be displayed.

In step 14, a composite image of the first and second datasets is formed based on the transparency of the second dataset. To form the composite image, a visual representation is selected for each dataset.

Figure 8:
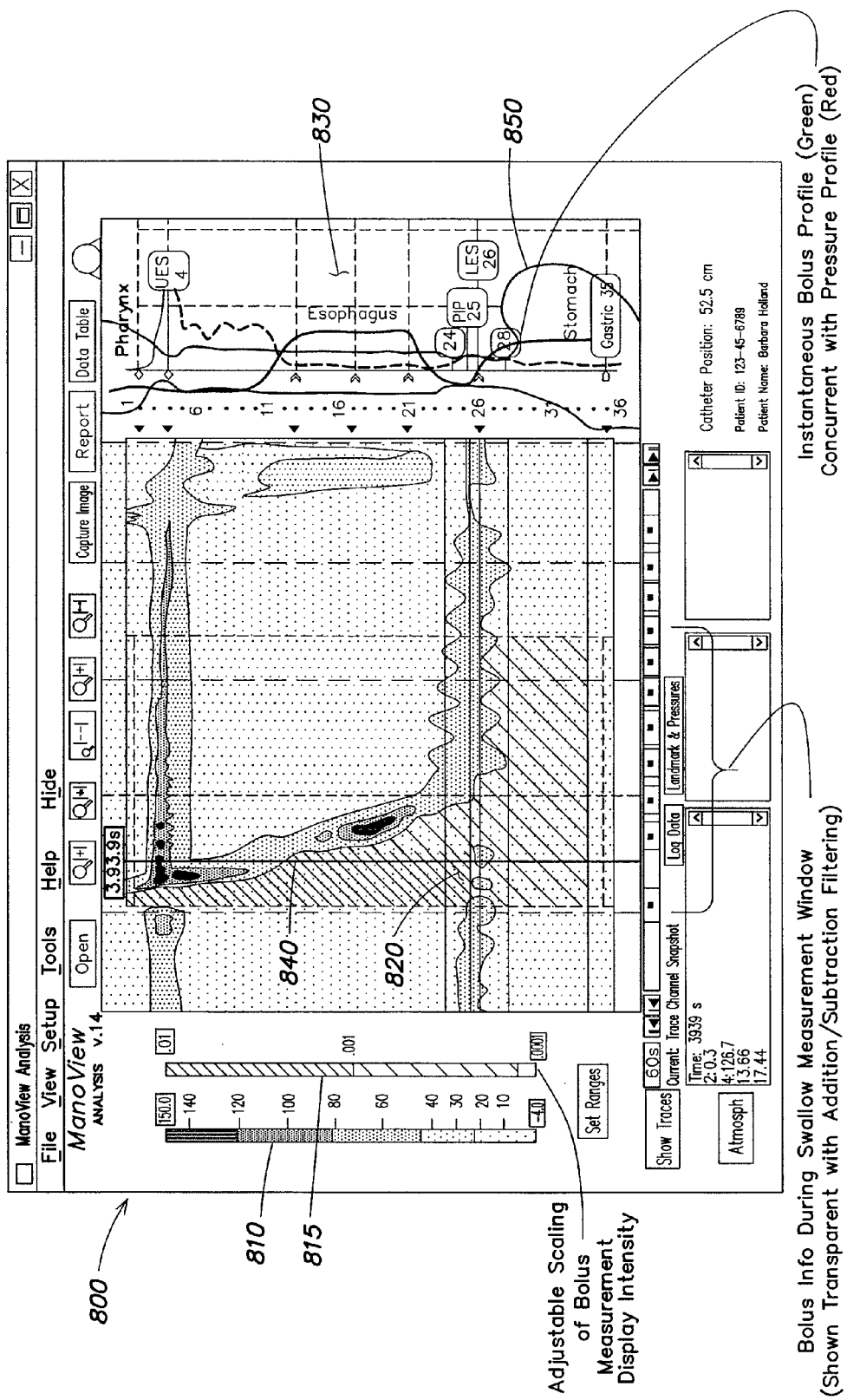
FIG. 8 is an embodiment with a first dataset and a second dataset displayed, each according to a respective color map, on a first plot with two coordinate axis, the second dataset partially transparent, and a second plot with one coordinate axis, the second plot display corresponding to a time determine by a time selector.

In some embodiments the first and/or second datasets may be represented according to corresponding color maps (e.g., pressure color map 110 and conductance color map 120 in legend 100, FIG. 2A). A color map indicates colors used to represent data values. Color maps may appear as a continuum of colors, each color being mapped to a data value, or as a discrete set of colors, each color representing an interval of data values. Color maps may appear as a transition between two or more colors. In one example, a color map transitions gradually from blue to green to yellow to red, and the dataset is represented by blue at a minimum value, by red at a maximum value, by green at a first intermediate value, and by yellow at a second intermediate value greater than the first. Color maps 810 and 815 are used in the embodiment 800 in the display of plot 820 (FIG. 8).

In FIGS. 2B-2C and FIGS. 3-7, datasets are represented by discrete color maps according to legend 100 (FIG. 2A). In these drawings, each pattern may represent a unique color. These drawings include a limited number of colors, each corresponding to a relatively wide range of values. However, such a depiction is for simplicity of illustration and is not a limitation of the invention. Any suitable number of colors may be included in a color map and each color may be mapped to a small range of values. It should be appreciated that in many embodiments, a sufficient number of colors may be included in a color map to create the appearance of a continuum of colors. Though, it is not necessary that either or both datasets be represented by multiple colors. For example, one of the datasets may be depicted using a single color. For example, a single color may be used with varying transparency to represent ranges of values.

As depicted in the attached figures, the datasets may be displayed with visually distinctive representations. Where color maps are available for each dataset, visual distinctiveness may be achieved by using different, and substantially non-overlapping colors to represent each dataset. However, the invention is not limited to creating visually distinctive representations for the dataset using different color maps.

Various combinations of visual representations may be used for the datasets. In some embodiments, where both datasets are each represented by a different color map, the composite image may be formed by determining, at some or all coordinates to be displayed, a display color. The display color is determined by mixing the colors from the respective color maps based on the transparency of the corresponding coordinate. The compositing calculation may be made as is known in the art or by any other suitable means.

In some embodiments where the transparency at a coordinate indicates that the second dataset is to be fully transparent as displayed, the display color may simply be the color representing the value of the first dataset. Conversely, at a coordinate where the transparency of the second dataset indicates that the second dataset should be fully opaque, the displayed color may be the color associated with the value of the second dataset (e.g., embodiment 500, FIG. 5). Though, at coordinates where the transparency is neither fully transparent or fully opaque, the displayed color may correspond to a color determined by blending colors representing the value of the first dataset and the value of the second dataset at that coordinate. Techniques as known in the art for blending colors may be used, though any suitable technique may be employed. This approach for representing two data sets may be applied, regardless of the number of degrees of freedom of the data.

Figure 6:
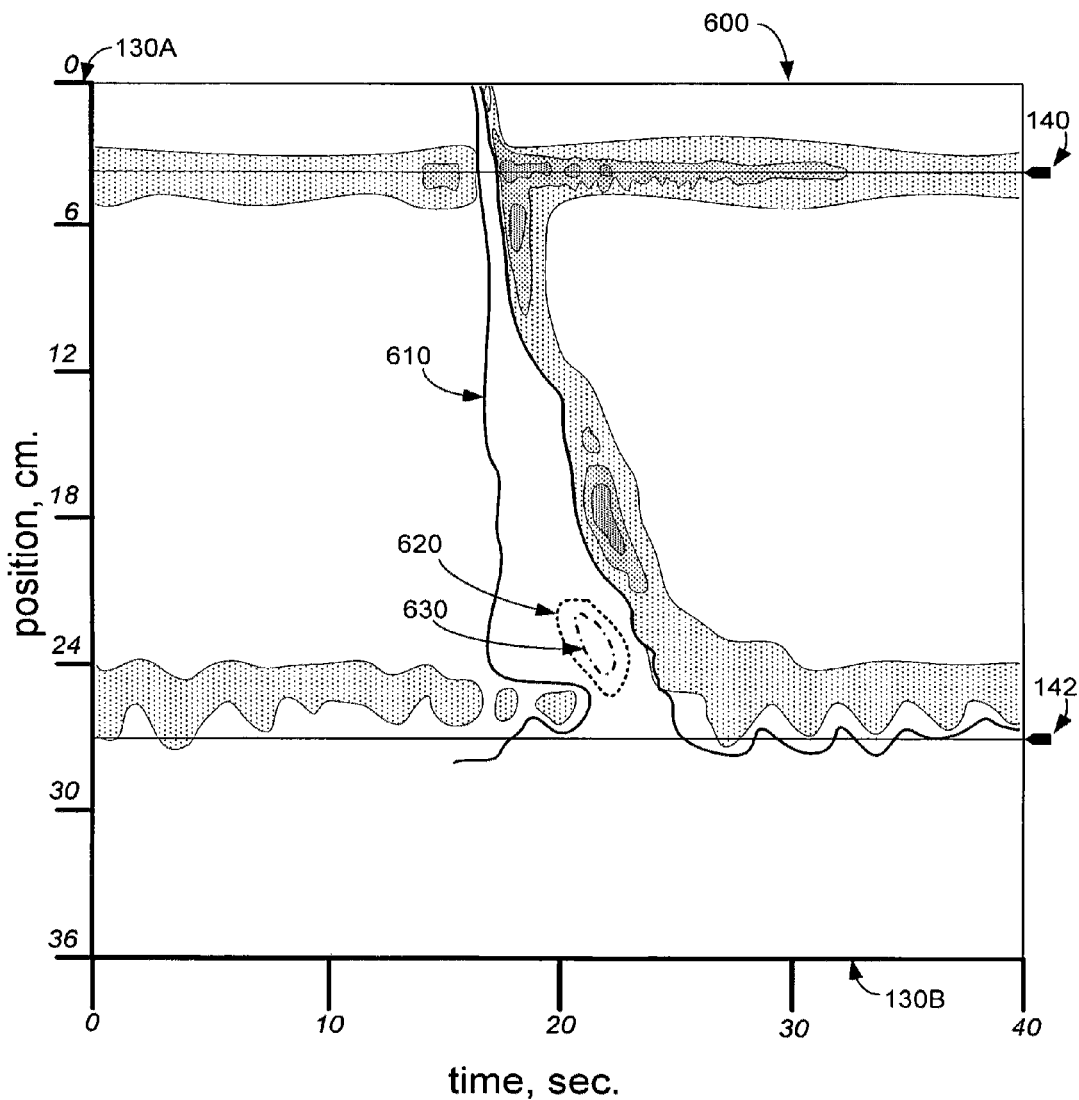
FIG. 6 is an embodiment with two datasets displayed, the first according to a color map and the second by way of contour lines, on a single plot with two coordinate axis.

In another embodiment, the first dataset is represented by a color map, and the second dataset is represented by contour lines (e.g, embodiment 600, FIG. 6). The composite image may formed by rendering contour lines at the coordinates designated to be opaque in step 13. The contour lines may be rendered with a color corresponding to the values represented by those lines. However, as noted above, the invention is not limited to display of values in color.

In step 15 the composite image is displayed. As should be apparent to one of skill in the art from the attached figures, the display may be rendered by a computer on a display device, though any suitable device may be used. Regardless of how displayed, visually, in the composite image the second dataset may appear superimposed on the first dataset. The composite image may be displayed in the context of a user interface to the computer used to display the datasets. The user interface may include features that provide a user the ability to modify aspects of how method 10 is performed. Such control features may implemented as controls provided by the above mentioned ManoScan™ and ManoView™ software. However, any suitable control mechanisms many be included In step 16 a depiction of the bodily lumen is optionally displayed (e.g., embodiment 220, FIG. 2B; embodiment 700, FIG. 7). For example, when the bodily lumen is the upper GI tract, the depiction may include reference features such as the pharynx, UES, esophagus, LES, stomach, and the like. The display, for example, may be initiated by a user interacting with controls that are provided by the user interface. Other controls may alter the appearance of the depiction of the anatomical features.

In step 17 controls for movement of anatomical landmarks are optionally displayed (e.g., controls 140 and 142 of embodiment 220, FIG. 2B and embodiment 500, FIG. 5) as part of the user interface of the computer. These user adjustable controls may be provided as indicators of anatomical landmarks that can be discerned from displayed data. If the depiction of the bodily lumen in step 16 is performed, the depiction may be adjusted to correspond with the position of the controls. In some embodiments, the anatomical landmark controls may be displayed along with guidelines across the data displayed in step 15 to facilitate a user positioning the indicators.

Figure 5:
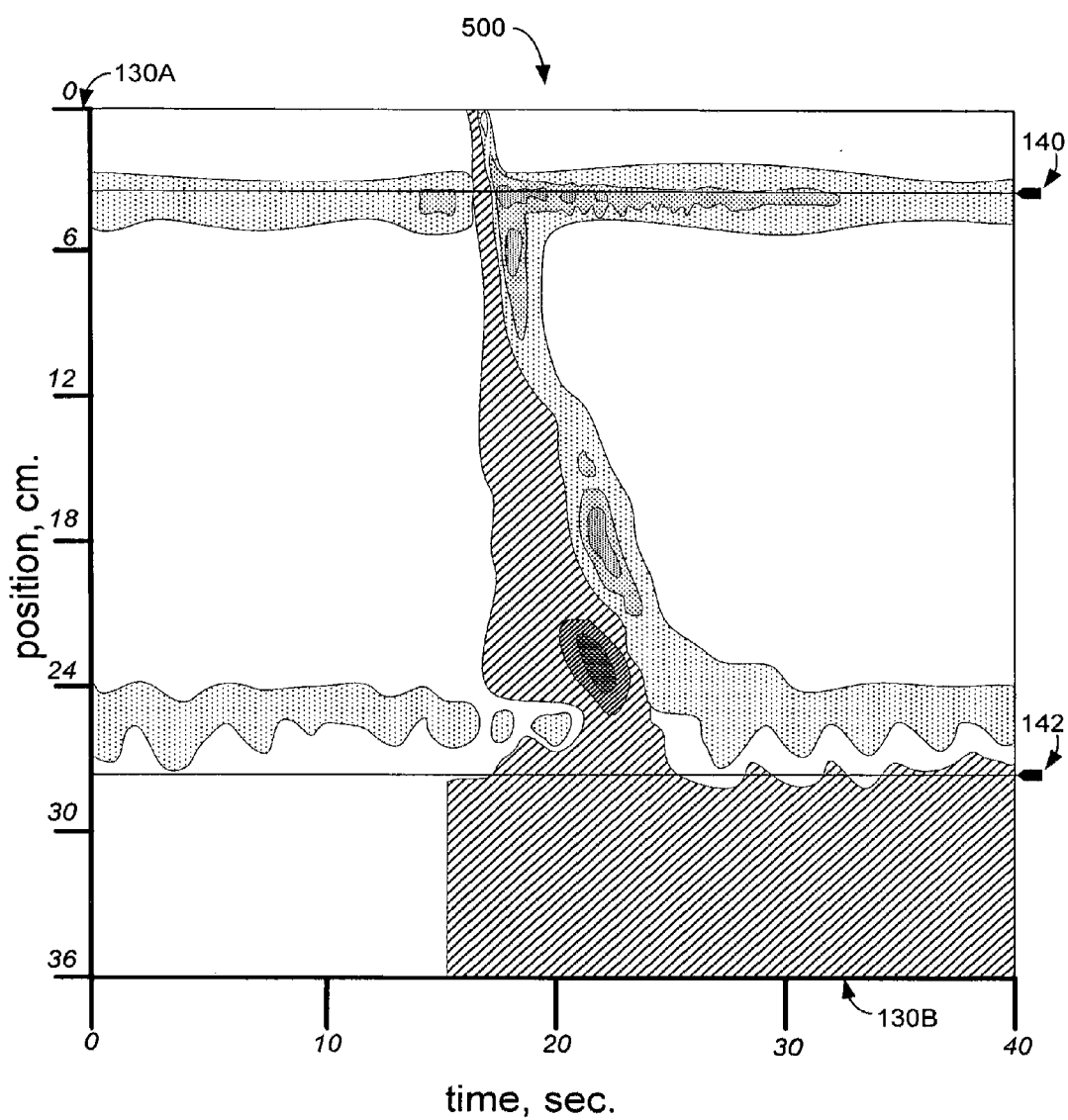
FIG. 5 is an embodiment with two datasets displayed, each according to a respective color map, on a single plot with two coordinate axis.

In some embodiments, the composite image displayed as a result of performing method 10 may present two sets of high-resolution physiological data such that the data are co-registered with respect to a position and time axis (e.g., embodiment 500, FIG. 5). The spatiotemporal relationship between the first and second datasets are maintained. Display of physiological data according to method 10 may ease the interpretation of physiological data and the diagnosis of a patient.

Method 10 may be implemented in any suitable way. For example, method 10 may be implemented through software code executable on a computing device using coding and display techniques as known for implementing data and analysis software, such as ManoScan™ data acquisition software and ManoView™ data analysis software. However, the specific mechanism by which the software is implemented is not critical to the invention. The software package may be stored on a computer storage medium encoded with instructions that, when executed by a computer system, perform the method 10.

It should be appreciated that method 10 may be adapted to display more than two datasets.

Having provided an overview of method 10, the example embodiments are describe in further detail.

Embodiments for Datasets Having Two Degrees of Freedom

Embodiments with datasets having two degrees of freedom are now presented.

One degree of freedom corresponds to a coordinate axis common to each dataset, and the other corresponds to a data value. In these examples, the spatial relationship between measured properties is preserved and may be shown against the correctly positioned anatomical depiction. The illustrated displays may be displayed alone or may be displayed in conjunction with other displays. For example, as illustrated by FIG. 8, below, a display with two degrees of freedom may be displayed in conjunction with a display having three degrees of freedom. The display with two degrees of freedom may represent a portion of data along an axis in the display with three degrees of freedom. As a specific example, the display with two degrees of freedom may represent data for a specific time in the plot with three degrees of freedom.

These displays may be static or dynamic. If static, the display with two degrees of freedom may represent values at a user specified time. If dynamic, the appearance of the display with two degrees of freedom may change over time.

Each example presented is provided in the context of a pressure and conductivity measurement inside the upper GI tract. However, this is simply exemplary, and any suitable source or type of data may be used. Measurement data of this type is indicative of peristaltic movements of a bolus through the upper GI tract including the esophagus. This data may, for example, be collected from a patient using a catheter with sensors to record pressure and conductivity measurements while a patient swallows a predetermined amount of water or other fluid.

Figure 2B:
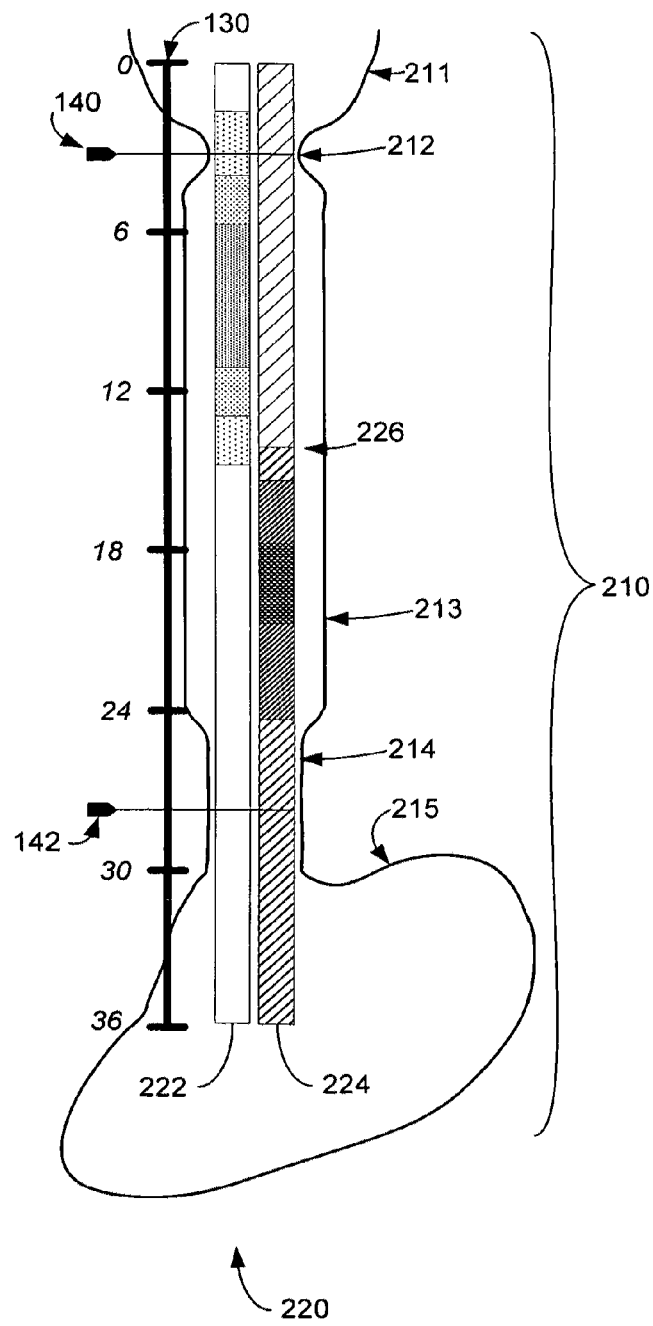
FIG. 2B is an embodiment with two datasets displayed adjacent to one another, each according to a respective pattern map.

In these example embodiments, the datasets each have a positional coordinate. FIGS. 2B-2C show example embodiments where the datasets consist of manometry and conductance data collected along the length of an elongated catheter inside an esophagus. The manometry and conductance data are represented by the color map shown in plot legend 100 in FIG. 2A. The plot legend 100 has a pressure color map 110 and conductance color map 120. For visual distinctiveness and clarity, the colors of the pressure color map 110 are represented by patterns with increasing concentration of polka dots while the colors of the conductance color map 120 are represented by patterns with increasing concentration and/or thickness of diagonal lines. However, this representation is selected for simplicity and any suitable representation for values may be used.

The pressure color map 110 illustrates the range of pressure measurement values. In order to focus on different aspects of the pressure measurement dataset, some embodiments of a user interface may have an upper limit control 114 and a lower limit control 112. In the example of legend 100, the upper and lower limits controls are text fields or other display controls through which a user may enter a value. The color map may be scaled to these limits. Here the lower limit 112 and upper limit 114 have been assigned 0 and 160 mmHg, respectively. In some other embodiments the color map may be scaled to the minimum and maximum values in the dataset or in any other suitable way.

Similarly, the conductance color map 120 illustrates the range of the conductance measurements. The colors of the conductance color map are distinct from the pressure color map. Here the lower limit 122 and upper limit 124 may also be adjustable. Here they are assigned values of $10^{-4}$ and $10^{-2}$ S, respectively.

The scale of each dataset's legend may be adjusted to represent the dataset in an appropriate way. For example, the scale may be linear such as for pressure color map 110 or logarithmic such as for conductance color map 120.

With the coordinate systems of each dataset correlated according to step 12, in some embodiments the data values are presented side-by-side in two adjacent bars. An illustrative example is provided by adjacent embodiment 220 in FIG. 2B. The adjacent embodiment 220 shows a manometry data plot 222 and conductance data plot 224 side-by-side. Illustrative manometry and conductance data is represented according to the pressure color map 110 and conductance color map 120, respectively (FIG. 2A). A coordinate axis 130 may be provided alongside the data plots to provide coordinate information.

In some embodiments, an illustration of anatomy of the region where measurements were taken may be shown along with the data. In the example adjacent embodiment 220, the measurement data is collected along the upper gastrointestinal (GI) tract which is illustrated as reference rendering 210. The reference rendering 210 may have a number of reference features to clearly illustrate the position of the measurement data relative to important features of the surrounding area. In the example where reference rendering 210 is the upper GI tract, the reference features may include the pharynx 211, UES 212, esophagus 213, LES 214, and stomach 215.

As illustrated in FIG. 2B, a user interface presenting an illustration of anatomy may have one or more landmarks, such as landmarks 140 and 142, associated with the illustration. The landmarks may act as control features, allowing a user to specify the location of the certain portions of the anatomy relative to the axis 130. A user, for example, could position these landmarks based on displayed data. By correlating the illustration to the specified location of the landmarks, the illustration of the anatomy may be scaled and positioned relative to coordinate axis 130 for the specific situation, e.g., patients of different sizes.

Embodiment 220 shown in FIG. 2B shows plots side-by-side. However, the inventors have appreciated that in many datasets certain correlations exist that enable multiple datasets to be meaningfully combined in an overlapping display area. Such correlations may exist, for example, in datasets where pressure and conductance indicate the position of a bolus. As illustrated in embodiment 220 (FIG. 2B), at points above a transition point 226, the pressure data is relatively large. Below the transition point 226, the pressure is relatively small. The conductance data, however, is relatively large below transition point 226, and relatively small above the transition point. Accordingly, it is possible to overlay the representation of the datasets without obscuring features of either data set likely to be used by a clinician analyzing the data.

A combined embodiment 230 is provided in FIG. 2C. In the combined embodiment 230 the manometry data and conductance data are combined onto a single data plot 232 here illustrated as a bar plot. In this example a threshold 126 (see FIG. 2A) associated with the conductance data (here the second dataset) is used to determine which data is displayed according to steps 13 and 14 of method 10 (FIG. 1). In this example, only conductance data with values above the threshold 126 is displayed in combined embodiment 230 (FIG. 2C). In regions where the conductance data is below the threshold, pressure data is displayed. Put another way, on data plot 232, conductance information is displayed if it exceeds the threshold 126, otherwise the pressure data is displayed. Like the adjacent embodiment 220 (FIG. 2B), the combined embodiment 230 is optionally displayed with coordinate axis 130 and reference rendering 210.

Another embodiment for displaying two types of physiological data is the line plot embodiment 240 illustrated in FIG. 2D. The illustrative example of pressure and conductance data are again illustrated, but here they are shown as lines 244 and 246, respectively, on data plot 242. Again coordinate axis 130 and reference rendering 210 are optionally displayed to provide context for the data.

Figure 2E:
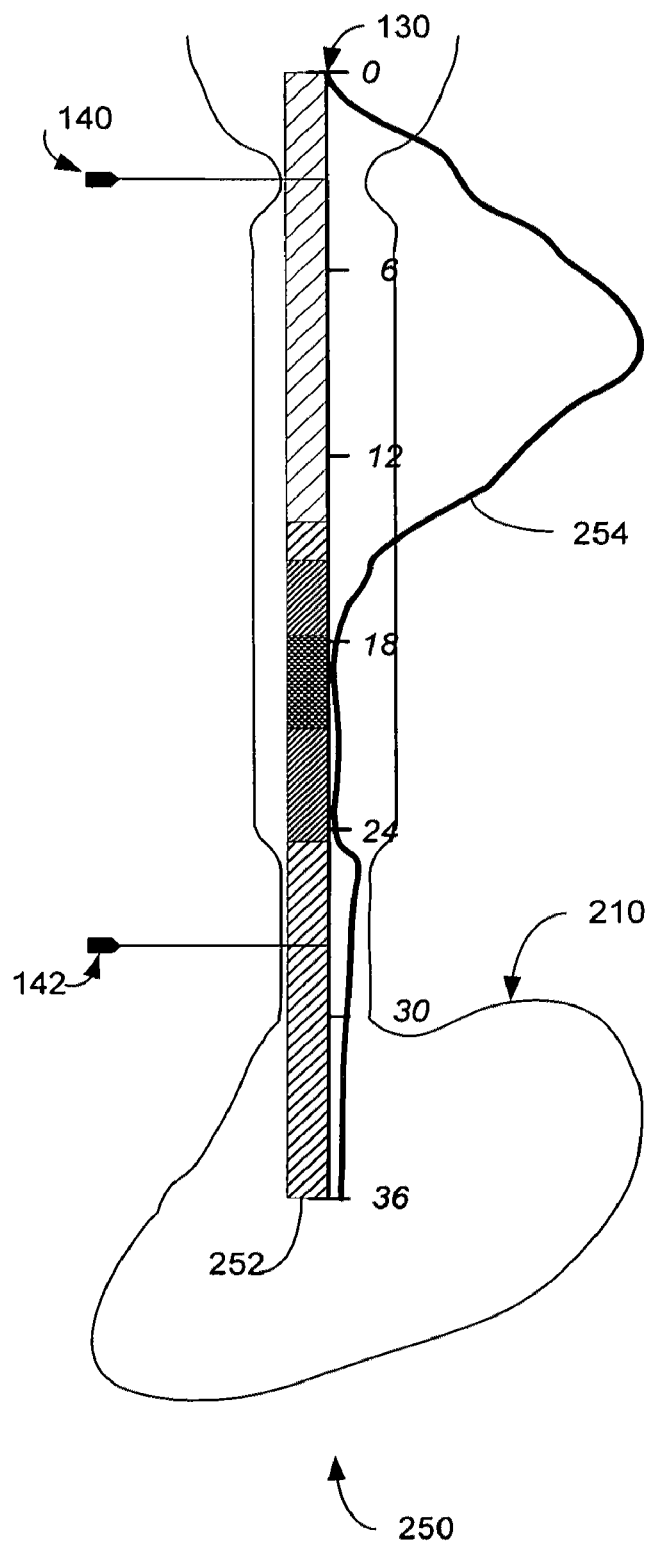
FIG. 2E is an embodiment with two datasets displayed on a single plot with one coordinate axis, the first according to a pattern map and the second as a data line.

As yet another embodiment for displaying data with two degrees of freedom, data may be displayed in mixed formats. As an example, a mixed plot embodiment 250 is shown in FIG. 2E. Here pressure data is displayed as line 254 and bolus data is displayed as a bar plot 252. Again coordinate axis 130 and reference rendering 210 are optionally displayed to provide context for the data.

It should be appreciated that while the data in embodiments 220, 230, and 250 displayed some or part of the data in accordance with a color map, a pattern map or any other suitable representation or combination of representations may be used. It is preferable the representation of the first dataset and the second dataset be visually distinctive. Visual distinction may be achieved, for example, by using different color maps and/or pattern maps (embodiment 230, FIG. 2C) or different line patterns (embodiment 240, FIG. 2D). Though, embodiment 250 (FIG. 2E), in which a bar plot is used for one dataset and a line plot is used for another dataset, illustrates that visual distinctiveness may be achieved in other ways.

Embodiments for Datasets Having Three Degrees of Freedom

The data processing and display techniques described above may be applied to the display of multiple datasets each having three degrees of freedom, two of the degrees representing a coordinate position (e.g., in a space-time plane) and a third representing a data value. As with techniques for display of data with two degrees of freedom, these techniques may be used in a computer system rendering a display as part of a user interface to the computer system. The displays may be static, representing data at a user selected time or range of time. Alternatively, the data may be representing as a moving time plot in which data, representing measurements at later times, is added to one side of the display. As new data is added on one side, the previously presented data is shifted toward on apposite side. As new data is added, older data may be removed from the other side of the data.

Figure 3:
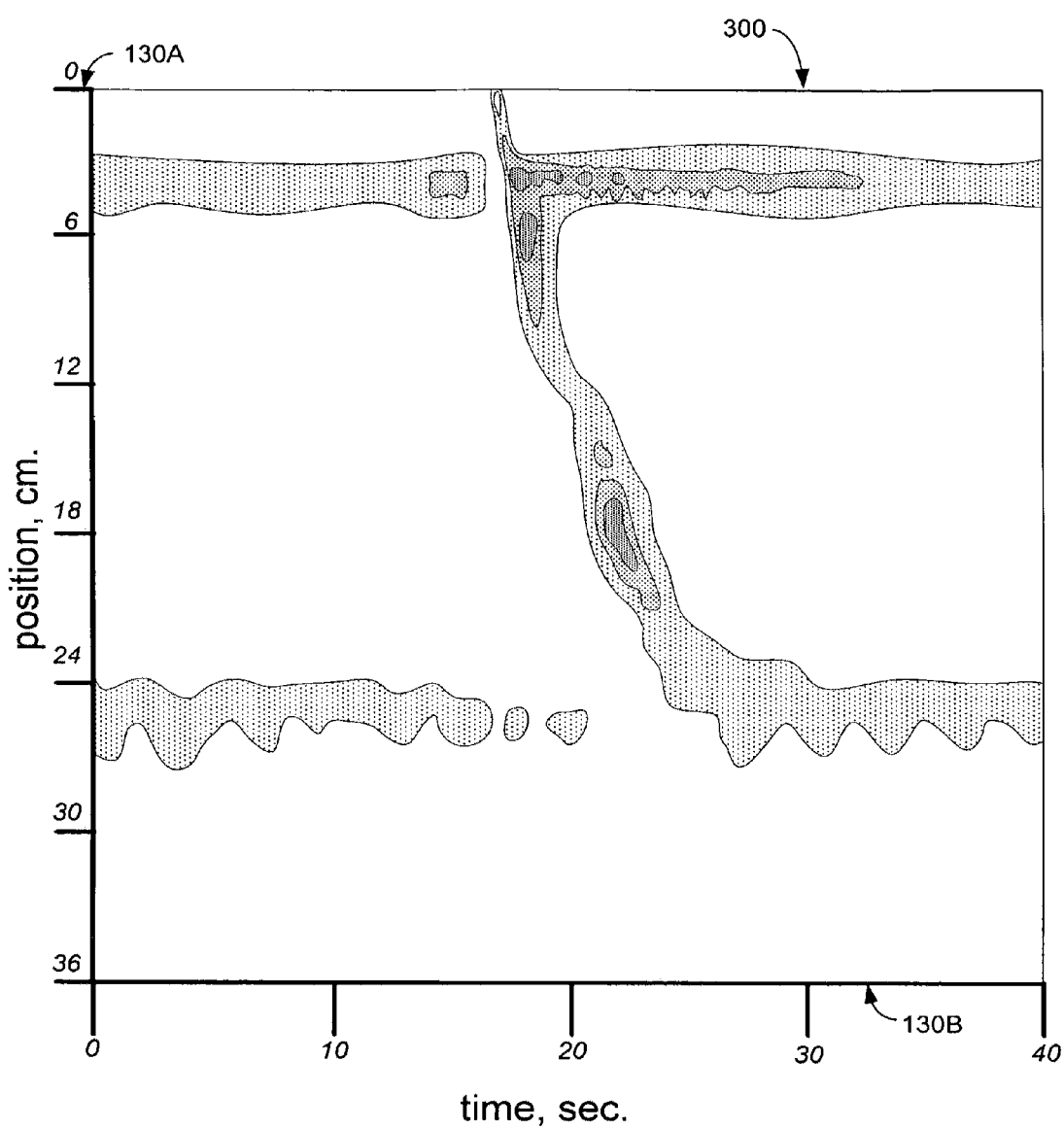
FIG. 3 is a spatiotemporal plot of a first dataset.

In FIG. 3, plot 300 presents pressure data as a function of position and time and shown according to pressure color map 110 (FIG. 2A). The two coordinate axes are position coordinate axis 130A and time coordinate axis 130B. The data from which plot 300 is created may constitute a first dataset.

Figure 4:
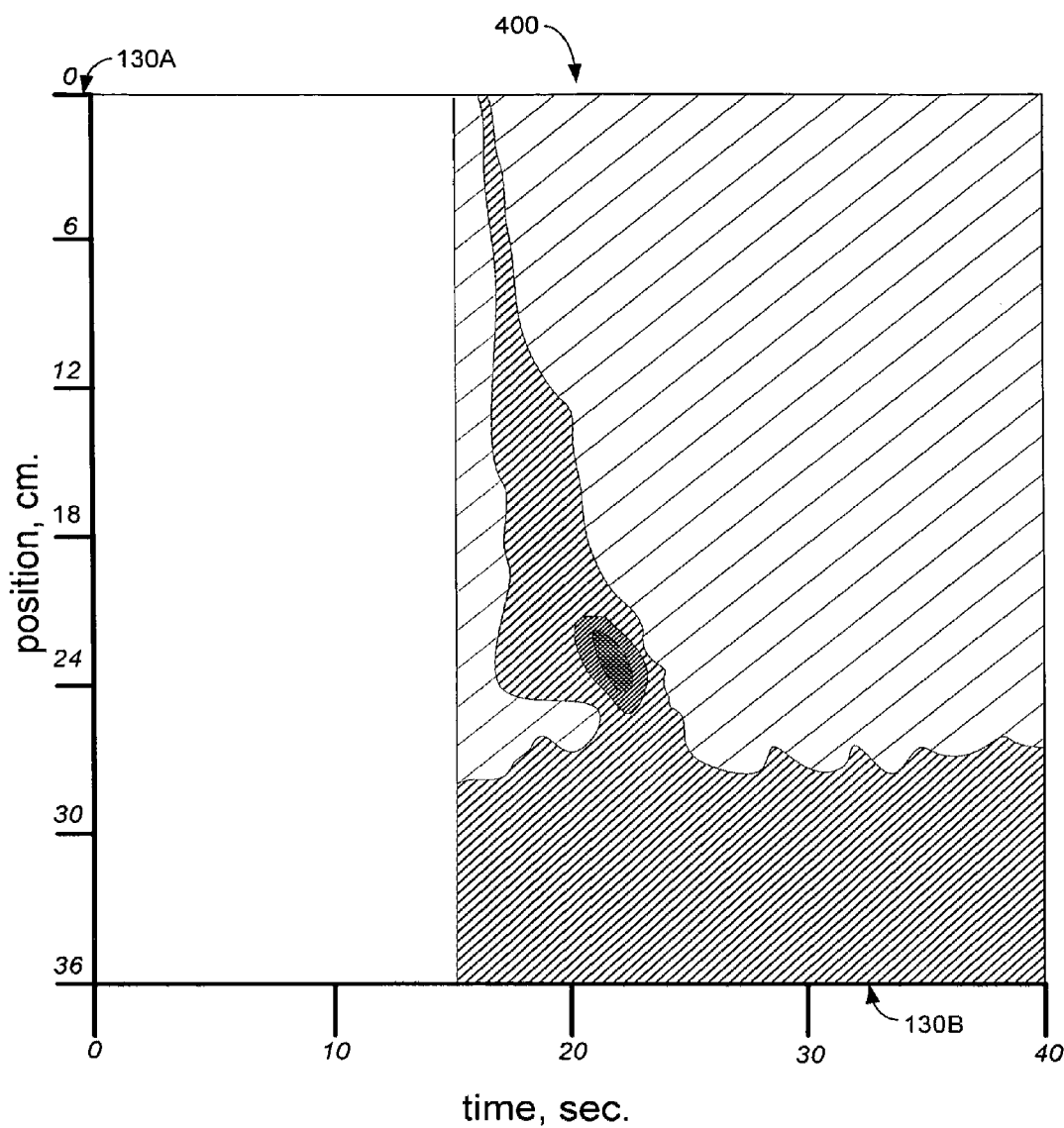
FIG. 4 is a spatiotemporal plot of a second dataset.

Similarly, in FIG. 4, plot 400 presents conductance data as a function of position and time and shown according to conductance color map 120 (FIG. 2A). The data from which plot 400 is created may constitute a second dataset. As illustrated the second dataset is collected over the same spatial region as the first dataset. Note that plot 400 illustrates conductance data collected in about a 25 second interval while plot 300 illustrates pressure data collected over a 40 second interval. However, in the example, the second interval is a subset of the 40 second interval. Thus the first dataset and the second dataset can be registered in time and space.

FIG. 5 illustrates plot 500, which illustrates the composite image formed by combining the data of plot 300 (FIG. 3) and plot 400 (FIG. 4) using the same technique used for forming plot 232 in the combined embodiment 230 (FIG. 2C). Namely, in plot 500 conductance information is displayed if it exceeds threshold 126 (FIG. 2A). At a space-time coordinate where the conductance data is below the threshold 126, the pressure data is displayed.

Any number of controls, such as controls 140 and 142, may be provided. In this example control 140 represents the position of the UES and control 142 represents the position of the LES. In some embodiments, a user may position the adjustors through a user interface based on displayed data such that the computer system rendering the display receives inputs that the system can use in correctly displaying an image of anatomical features.

In yet another embodiment, the data values of the second dataset are displayed as contours. Plot 600 in FIG. 6 displays the pressure dataset according to the pressure color map 110 (FIG. 2A) but now displays the conductance data as contours 610, 620 and 630 representing equally valued points of $10^{-3.5}$, $10^{-3}$, and $10^{-2.5}$ S/m, respectively. In plot 600 different line patterns are used to distinguish contour 610, 620 and 630. Any suitable way of distinguishing the lines may be used, such as line markers, colors, line patterns, or a combination of such elements. In some embodiments, the lines may be labeled with the data values they represent and/or a legend may be provided to indicate what each line represents.

Additional Embodiments

Figure 7:
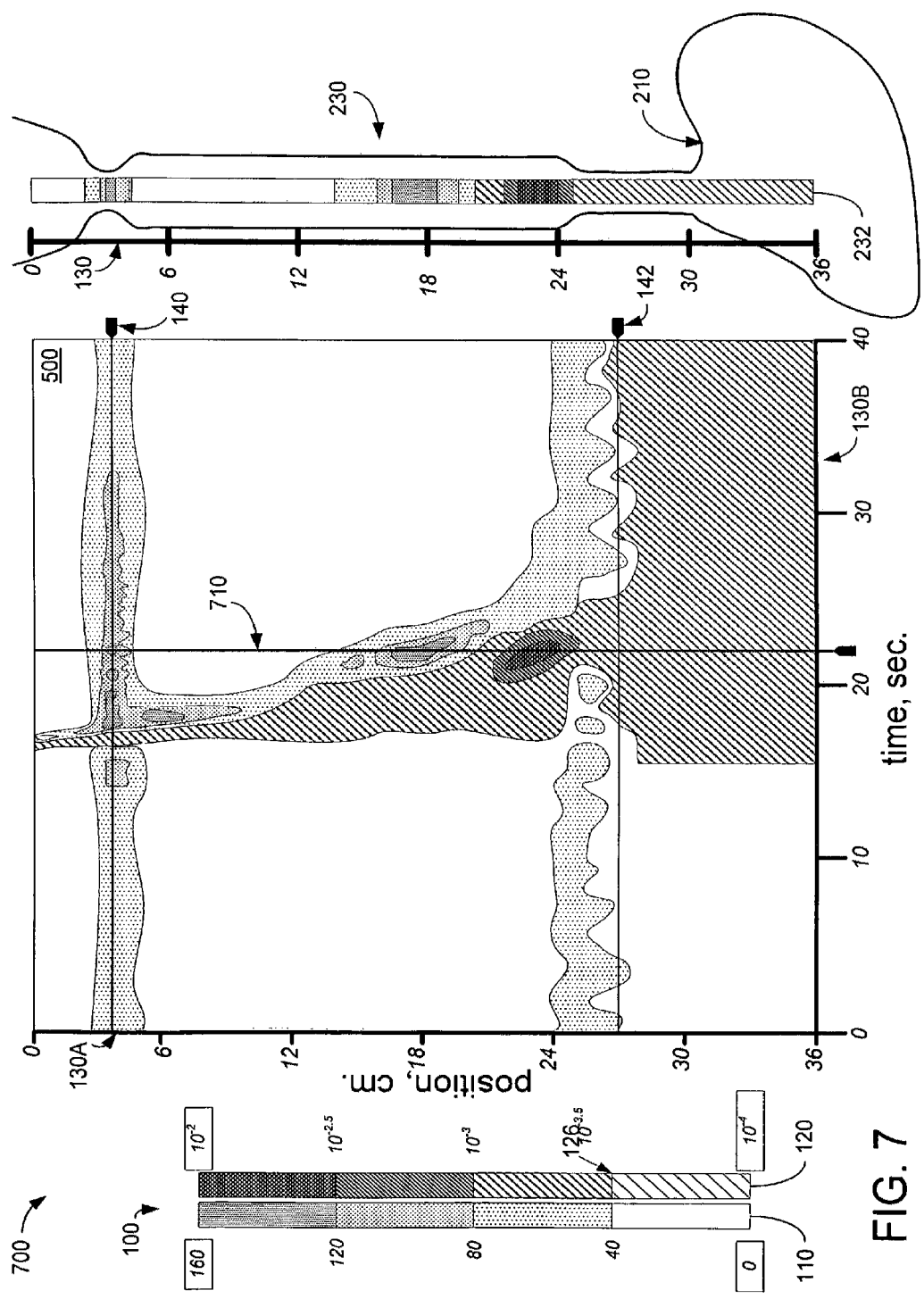
FIG. 7 is an embodiment with two datasets displayed, each according to a respective color map, on a first plot with two coordinate axis and a second plot with one coordinate axis, the second plot display corresponding to a time determine by a time selector.

An embodiment 700 is shown in FIG. 7 which combines embodiment 500 and embodiment 230, with the plot showing data with three degrees of freedom and the plot showing data with two degrees of freedom aligned along an axis representing a shared coordinate. In the embodiment illustrated, this shared coordinate is the spatial dimension along the lumen where measurements were made.

Embodiment 700 demonstrates that display techniques as described above may be used in a review mode for reviewing collected data. Coordinate axis 130 and position axis 130A both are for the same coordinate and are properly registered with one another. Embodiment 700 contains a time selector 710. The position of time selector 710 on the time axis 130B determines what data is rendered on single data plot 232. A user interface may provide a user the ability to select to the position of the time selector 710 on time axis 130B. When time selector 710 is repositioned, the single data plot 232 may be updated with data corresponding to the new position. While embodiment 230 is integrated into embodiment 700, any embodiment for datasets having two degrees of freedom may be used. For example, embodiments 220, or 240 may be used in place of embodiment 230. The measurement profiles of the profile presented in embodiment 230, the plot 500, and the anatomical depiction 210 all have identical scaling and orientation in the spatial dimension.

FIG. 8 illustrates an embodiment using the ManoView™ software user interface adapted to display bolus location information superimposed on manometry data. Color map 810 is used to represent a first dataset containing pressure data in plot 820. Color map 820 is used to represent a second dataset containing conductance data in plot 820. In this embodiment, color map 815 is a monochrome color map. In plot 820 the transparency of the representation of the second dataset decreases monotonically with the data value. Plot 830 displays pressure and conductance data corresponding to the position of time selector 840. The measurement profiles in plot 830, spatiotemporal plot 820, and anatomical depiction 850 all have identical scaling and orientation in the spatial dimension. Plot 820 may comprise data beyond the constraints of the plot window. The computer system rendering plot 820 may scroll the data across the display such that different windows in time are displayed. For example, plot 820 may scroll laterally along the direction of changing time. In some embodiments, plot 820 may scroll as additional values for the first dataset and/or second dataset are loaded. In other embodiments, the display may be scrolled in response to user input specifying a time to be displayed.

Systems for Performing Method 10

Figure 9:
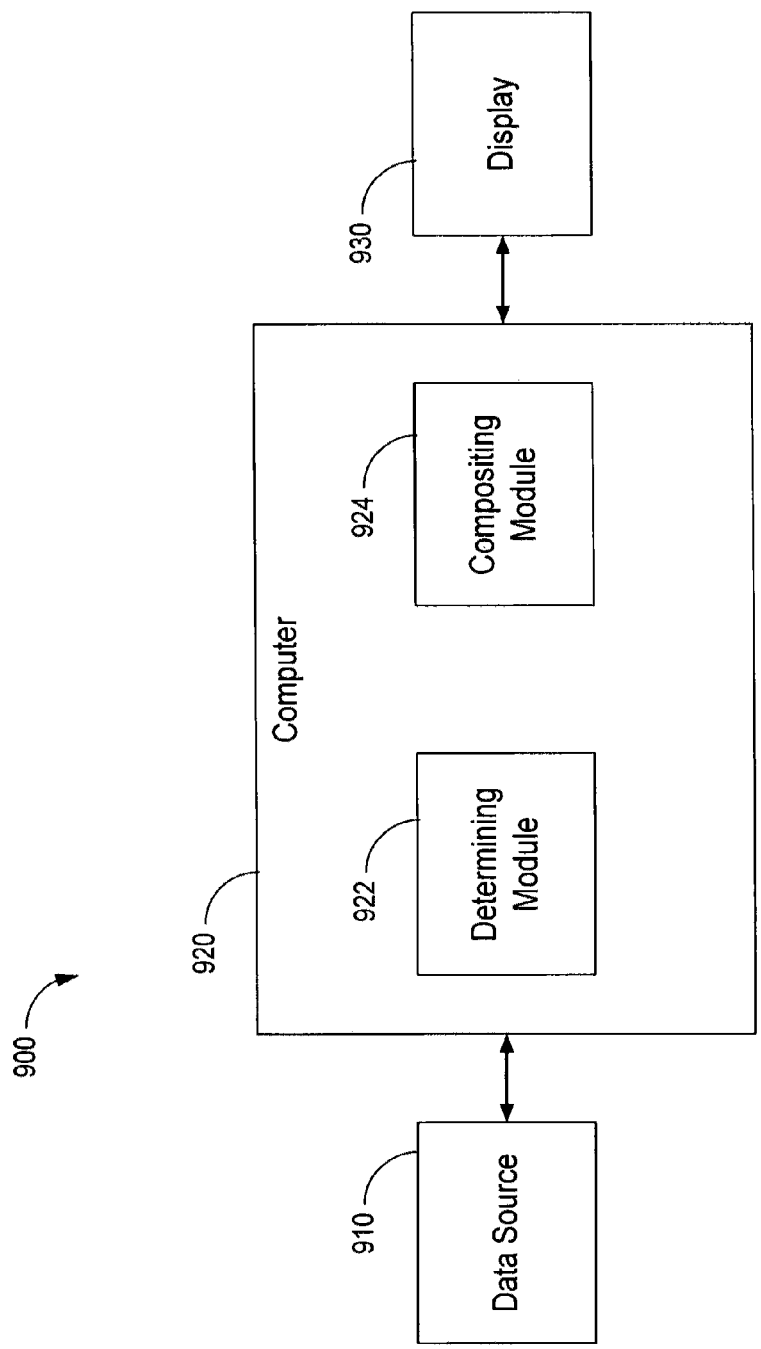
FIG. 9 is a system for performing the method according to an embodiment of the invention.

The above discussed software for data analysis and viewing may, as is known in the art, be executed on a system. Accordingly, method 10 (FIG. 1) may be implemented by the system 900 shown in FIG. 9. The system 900 includes a data source 910, a computer 920, and a display 930. The data source 910 provides the datasets to computer 920. In some embodiments, the data source 910 is a computer storage medium. In some embodiments, the data source 910 is a measurement device for performing experimental measurements. For example the data source 910 may be a catheter equipped with pressure and conductance sensors with appropriate drive electronics to perform measurements and transmit the measured values. The data source may provide datasets to computer 920 in real-time. For example, in an embodiment where data source 910 is a measurement device, the datasets may be provided in real-time to computer 920 such that computer 920 may process the datasets and output for display on display 930 before the physical parameters the datasets represent have significantly changed.

Computer 920 may be embodied by any suitable computing device. Example embodiments of computer 920 include a PC, a microprocessor, a laptop computer, a personal digital assistants (PDAs), and the like. Computer 920 contains a determining module 922 and compositing module 924 which may be implemented in hardware, software, or a combination of the two. Determining module 922 may perform step 13 of method 10. Compositing module 924 may perform step 14 of method 10. Computer 920 outputs the composite image formed in step 14 to display 930.

Display 930 may provide a visual presentation of the composite image according to step 15 of method 10.

Having thus described several aspects of at least one embodiment of this invention, it is to be appreciated that various alterations, modifications, and improvements will readily occur to those skilled in the art. For example, display information may be registered and combined.

As another example, the term "conductance" is used above. One of skill in the art will understand that impedance measurements, which are effectively the reciprocal of conductance measurements, also convey conductance information.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof to obtain and produce the displays of physiological data. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of displaying physiological data relating to a bodily lumen, the method comprising:
   providing a first dataset, the first dataset comprising a plurality of data values relating to a first property along the lumen during a time interval;
   providing a second dataset, the second dataset comprising a plurality of data values relating to a second property along the lumen during the time interval;
   correlating the first dataset and the second dataset in space and time;
   selecting a portion of the first dataset and a portion of the second dataset based on data values of the second dataset; and
   displaying on a plot, at least the selected portion of the first dataset and at least the selected portion of the second dataset as correlated in space and time, the selected portion of the second dataset being displayed using a representation that is visually distinct from a representation of the selected portion of the first dataset.

2. The method of claim 1, wherein the first dataset comprises values representing pressure within the bodily lumen.

3. The method of claim 2, wherein the second dataset comprises values representing impedance within the bodily lumen.

4. The method of claim 1, wherein providing a first dataset and providing a second dataset comprises:
   placing a catheter in the esophagus of a patient, the catheter comprising a plurality of pressure sensors and a plurality of impedance sensors having a predetermined positional relationship;
   obtaining the first dataset comprises measuring values with the plurality of pressure sensors; and
   obtaining the second dataset comprises measuring values with the plurality of impedance sensors.

5. The method of claim 4, wherein:
   the method further comprises providing a material to the patient to swallow; and
   obtaining of the first dataset and the obtaining of the second dataset are performed during the swallow.

6. The method of claim 1, wherein selecting the portion of the second dataset comprises selecting data values in the second dataset above a threshold.

7. The method of claim 6, wherein selecting the portion of the second dataset comprises selecting a portion of the first dataset that is mutually exclusive in a spatio-temporal coordinate system with the selected portion of the second dataset when the first dataset and the second dataset are correlated in space and time.

8. The method of claim 1, further comprising:
   displaying, in conjunction with the plot, a depiction of the bodily lumen with anatomical landmarks registered with a spatial axis of the plot.

9. The method of claim 1, wherein the plot is a first plot and the method further comprises:
   displaying on a second plot adjacent to the first plot, for a select measurement time, at least the selected portion of the first data corresponding to the select measurement time and at least the selected portion of the second data corresponding to the select measurement time.

10. The method of claim 1, wherein the plot is a first plot and the method further comprises:
displaying a second plot adjacent to the first plot, the second plot displaying a first portion of the first data corresponding to a select measurement time side-by-side with a second portion of the second data corresponding to the select measurement time.

11. The method of claim 10, wherein the second plot further comprises a spatial axis, and the method further comprises:
displaying a depiction of a bodily lumen with anatomical landmarks registered with the spatial axis.

12. The method of claim 1, wherein, in the displaying step, the selected portion of the first dataset is displayed according to a first color map and the selected portion of the second dataset is displayed according to a second color map, the second color map consisting essentially of colors not in the first color map.

13. The method of claim 12, wherein the second color map is monochromatic.

14. The method of claim 1, wherein, in the displaying step, the selected portion of the first dataset is displayed according to a color map and the selected portion of the second dataset is displayed as a contour line plot.

15. The method of claim 1, wherein the plot is a spatiotemporal plot comprising a distance axial direction and a time axial direction.

16. A computer storage device encoded with instructions that, when executed, perform a method for displaying physiological data, the method comprising acts of:
obtaining a first dataset representing pressure within a bodily lumen and a second dataset representing an electrical property within the bodily lumen;
forming a composite image including a two-dimensional spatiotemporal plot representing the first and second datasets as correlated in space and time by superimposing a representation of the first dataset and a representation of the second data set on the spatiotemporal plot, with the first dataset represented in a manner that is visually distinct from the manner in which the second dataset is represented; and
displaying the composite image.

17. The computer storage device of claim 16, wherein the obtaining comprises:
obtaining the first dataset by measuring the pressure within the bodily lumen; and
obtaining the second dataset by measuring conductance or impedance within the bodily lumen.

18. The computer storage device of claim 16, wherein the two-dimensional spatiotemporal plot represents the first and second datasets using different colors.

19. The computer storage device of claim 16, wherein the two-dimensional spatiotemporal plot comprises a contour plot.

20. The computer storage device of claim 16, wherein superimposing a representation of the first dataset and a representation of the second data set on the spatiotemporal plot comprises:
representing the first dataset in the composite image according to a first color map;
representing the second dataset in the composite image according to a second color map, the second color map being visually distinct from the first color map; and
determining display colors, within the at least a portion of the shared spatial region, by mixing first colors and second colors based on the transparency, the first colors representing physiological data values determined from the first dataset according to the first color map, and second colors representing physiological data values determined from the second dataset according to the second color map.

21. The computer storage device of claim 16, wherein displaying the composite image comprises displaying the first and second datasets co-registered in space and time.

22. The computer storage device of claim 16, wherein the two-dimensional spatiotemporal plot shows a time history of pressure and the electrical property.

23. The computer storage device of claim 16, wherein:
superimposing a representation of the first dataset and a representation of the second data set on the spatiotemporal plot comprises determining a transparency for at least one of the first and second datasets; and
the composite image is formed at least partially based on the transparency.

24. The computer storage device of claim 23, wherein determining the transparency comprises determining the transparency to dither the display of the second dataset.

25. The computer storage device of claim 23, wherein determining the transparency comprises determining the transparency based on physiological data values determined from the second dataset.

26. The computer storage device of claim 25, wherein the method further comprises:
displaying a second image adjacent to the composite image, the second image comprising a first representation of at least a portion of the first dataset at a selected measurement time and a second representation of at least a portion of the second dataset at the selected measurement time; and
registering spatial axes of the composite image and the second image.

27. The computer storage device of claim 26, further comprising:
depicting of a bodily lumen with anatomical landmarks registered with the spatial axes.

28. The computer storage device of claim 26, further comprising:
providing adjustable markers to position the anatomical landmarks.

29. The computer storage device of claim 25, wherein determining the transparency comprises setting the transparency to opaque at coordinates corresponding to positions of contour lines representing the second dataset.

30. A computer storage device encoded with instructions that, when executed, perform a method for displaying physiological data, the method comprising acts of:
obtaining a first dataset and a second dataset, the first dataset and the second dataset comprising measurements of different physiological properties in a shared spatial region;
determining a transparency of the second dataset within at least a portion of the shared spatial region;
forming a composite image comprising a visual representation of the first and second datasets based on the transparency; and
displaying the composite image,
wherein determining the transparency comprises determining the transparency based on physiological data values determined from the second dataset,
wherein forming the composite image comprises:
representing the first dataset in the composite image according to a first color map;

representing the second dataset in the composite image according to a second color map, the second color map visually distinct from the first color map; and determining display colors, within the at least a portion of the shared spatial region, by mixing first colors and second colors based on the transparency, the first colors representing physiological data values determined from the first dataset according to the first color map, and second colors representing physiological data values determined from the second dataset according to the second color map.

31. The computer storage device of claim 30, wherein:

determining the transparency comprises:

determining a first region, in the at least a portion of the shared spatial region, where the transparency is fully transparent;

determining a second region, in the at least a portion of the shared spatial region, where the transparency is opaque; and determining display colors comprises:

selecting first colors representing physiological data values determined from the first dataset in the first region; and selecting second colors representing physiological data values determined from the second dataset in the second region.

32. The computer-readable device of claim 30, further comprising the step of:

time synchronizing the first dataset and the second dataset.

33. A system for displaying physiological data related to a bodily lumen, the system comprising:

a data source of physiological data in the form of a first dataset and a second dataset, the first dataset representing pressure within a bodily lumen and the second dataset representing an electrical property within the bodily lumen;

a computer to receive the first dataset and second dataset from the data source and output a composite image, the computer comprising:

a compositing module for forming a composite image including a two-dimensional spatiotemporal plot representing the first and second datasets as correlated in space and time by superimposing a representation of the first dataset and a representation of the second data set on the spatiotemporal plot, with the first dataset represented in a manner that is visually distinct from the manner in which the second dataset is represented; and a display to display the composite image output from the computer.

34. The system of claim 33, wherein the data source comprises a catheter comprising a plurality of pressure sensors and a plurality of impedance or conductance sensors having a predetermined positional relationship.

35. The system of claim 33, wherein:

the compositing module further forms a second image representing the first dataset and the second dataset at a select time; and the display displays the second image registered with a spatial axis of the composite image.

36. The system of claim 33, wherein:

the composite image comprises a temporal direction and a spatial direction; and the display scrolls the composite image in an axial direction.

37. The system of claim 33, wherein the electrical property is at least one of impedance and conductance.

38. The system of claim 33, wherein the two-dimensional spatiotemporal plot represents the first and second datasets using different colors.

39. The system of claim 33, wherein the two-dimensional spatiotemporal plot comprises a contour plot.

* * * * *